US011382570B1

(12) United States Patent
Singh et al.

(10) Patent No.: US 11,382,570 B1
(45) Date of Patent: Jul. 12, 2022

(54) ENCRYPTED SECURITIZED DATABASES FOR DEVICES AND SYSTEMS THAT MEASURE, QUANTIFY, COMPARE, PACKAGE, AND CAPTURE DATA

(71) Applicants: Ravindra Pratap Singh, Irvine, CA (US); Daniel Maurice Lerner, Virginia Beach, VA (US)

(72) Inventors: Ravindra Pratap Singh, Irvine, CA (US); Daniel Maurice Lerner, Virginia Beach, VA (US)

(73) Assignee: NFT IP HOLDINGS LLC, Irvine, CA (US)

( * ) Notice: Subject to any disclaimer, the term of this patent is extended or adjusted under 35 U.S.C. 154(b) by 0 days.

(21) Appl. No.: 17/649,766

(22) Filed: Feb. 2, 2022

Related U.S. Application Data

(63) Continuation of application No. 17/354,785, filed on Jun. 22, 2021, now Pat. No. 11,272,888.

(51) Int. Cl.
*G06K 9/00* (2022.01)
*A61B 5/00* (2006.01)
(Continued)

(52) U.S. Cl.
CPC .......... *A61B 5/7267* (2013.01); *A61B 5/7275* (2013.01); *A61B 5/7282* (2013.01);
(Continued)

(58) Field of Classification Search
CPC .. G01N 33/4972; G01N 33/497; G01N 33/18; G01N 33/1826; G01N 33/98;
(Continued)

(56) References Cited

U.S. PATENT DOCUMENTS 9,875,510 B1   1/2018   Kasper
9,947,015 B1   4/2018   Vildosola et al.
(Continued)

FOREIGN PATENT DOCUMENTS

CN   104573030 A    4/2015
DE   10202001536 A1   10/2020
(Continued)

OTHER PUBLICATIONS

Liu, "Deep Learning versus Professional Healthcare Equipment: A Fine-Grained Breathing Rate Monitoring Model Bang," Nov. 2017, Hindawi (Year: 2017).*
(Continued)

*Primary Examiner* — Alex Kok S Liew
(74) *Attorney, Agent, or Firm* — ePatentManager; Guerry L. Grune

(57) ABSTRACT

Data obtained by computer processing device(s) includes human biological change data from event data stream(s) and dynamic marketplaces allowing for ranking change(s). The data can correlate biological change data with ranking statistics from an event such that the correlation identifies and measures a magnitude of change of human biological responses from data acquired from event data stream(s). The correlation of human biological change data and/or dynamic changing marketplace data with ranking statistics creates object(s) for storage and analysis within database(s), wherein the objects possess time synchronized responses before, during or after events. These objects can be packaged with a Packager such that the Packager extracts data from data set(s) wherein data is contained in data sets as data slices and/or other data subsets optionally contained in these objects allowing selectivity of data sets according to desired types and intensities of change(s) of a magnitude determined and measured by the devices.

30 Claims, 3 Drawing Sheets

(51) Int. Cl.
  *G06N 3/08* (2006.01)
  *G06K 9/62* (2022.01)
  *G06F 16/28* (2019.01)

(52) U.S. Cl.
  CPC .......... *A61B 5/7292* (2013.01); *G06F 16/285* (2019.01); *G06F 16/288* (2019.01); *G06K 9/6256* (2013.01); *G06N 3/08* (2013.01)

(58) Field of Classification Search
  CPC .......... G01N 2033/4975; A61B 5/0022; A61B 5/0205; A61B 5/746; A61B 5/4845; A61B 5/7405; A61B 2562/0219; A61B 5/024; G16H 40/67; G16H 10/60; G16H 50/20; G16H 40/63; G16H 20/17
  See application file for complete search history.

(56) References Cited

U.S. PATENT DOCUMENTS

| | | | |
|---|---|---|---|
| 10,505,726 B1 | 12/2019 | Andon et al. | |
| 10,594,638 B2 | 3/2020 | Bostick et al. | |
| 10,904,183 B2 | 1/2021 | Bostick et al. | |
| 11,272,888 B1 * | 3/2022 | Singh | G06F 16/288 |
| 2013/0002683 A1 | 1/2013 | Li et al. | |
| 2014/0334653 A1 * | 11/2014 | Luna | H05B 47/115 600/27 |
| 2018/0218379 A1 | 8/2018 | Ono | |
| 2019/0050117 A1 * | 2/2019 | Coulthard | G06T 11/206 |
| 2019/0299105 A1 | 10/2019 | Knight et al. | |
| 2020/0073485 A1 | 3/2020 | Al-Halah et al. | |

FOREIGN PATENT DOCUMENTS

| | | |
|---|---|---|
| JP | 2005199403 A | 7/2005 |
| JP | 2015169702 A | 9/2015 |
| WO | 2012094725 A1 | 7/2012 |
| WO | 2019069910 A1 | 4/2019 |
| WO | 2020067633 A1 | 4/2020 |

OTHER PUBLICATIONS

Liu, Deep Learning versus Professional Healthcare Equipment: A Fine-Grained Breathing Rate Monitoring Model, Mar. 2018, Hindawi (Year: 2018).

* cited by examiner

ENCRYPTED SECURITIZED DATABASES FOR DEVICES AND SYSTEMS THAT MEASURE, QUANTIFY, COMPARE, PACKAGE, AND CAPTURE DATA

PRIORITY

This application is a continuation of and claims priority to U.S. Nonprovisional application Ser. No. 17/354,785 filed Jun. 22, 2021, entitled "Devices and Systems that Measure, Quantify, Compare, Package, and Capture Human Content in Databases".

The above-mentioned application is hereby incorporated by reference in its entirety.

BACKGROUND

The present disclosure relates to the field of electronic communications, and specifically to the field of electronic data from human biological responses captured, organized, and analyzed using data bases for data storage and retrieval. Still more specifically, the present disclosure relates to the field of conveying biological responses via electronic data during the course of an event.

In multi event sessions, such as those provided and captured by the use of smart phones, tablet computers, etc., these devices allow one or more parties to communicate. Such event sessions often allow a set of events between two or more parties to be displayed on the user interface of such communication devices, thereby providing a chronological record of the event exchanges between the parties.

However, an event alone can be ambiguous. For example, consider the event captures a biological response such as "I am so happy". If spoken aloud, an emphasis on different words during the event can dramatically alter the meaning of the event. For example, if the word "I" is emphasized (i.e., is stressed when the phrase/sentence is spoken aloud), then the event implies that the speaker is the only person from a group who is happy. If the word "am" is emphasized when spoken aloud, then the event implies that the speaker is rebutting a challenge that he/she is not really happy. If the word "so" is emphasized when spoken aloud, then the phrase during the event may be interpreted as being sarcastic. If the word "happy" is emphasized, then the event may be interpreted as the speaker truly being ecstatic.

In order to convey what the event truly means to the experiencer or participant of the event various approaches have been used and described in related prior art.

For example, U.S. Patent Application Publication No. 2013/0002683 describes a method for augmenting text messages with biological response icons (i.e., "emoticons"), which are selected from a predefined set of emoticons. However, such a system is limited to such predefined emoticons, which may or may not express the true biological response of the sender of the text message. Furthermore, emoticons are often trivialized, due to their cartoon-like features. That is, a recipient of an emoticon may consider the emoticon to be a "throw-away" addition that may or may not truly represent how the text message sender is feeling. Also, a user may select an emoticon that, unbeknown to even the sender of the text message, does not really portray how they are feeling.

Another approach to clarifying how a text message sender feels is to alter the appearance of the text message through bolding, underlining, color changing, etc. That is, the sender of the text message may simply bold or underline the first word of the text message "I am so happy" in order to emphasis that he/she, if nobody else in a group, is truly happy. Known prior art removes the task of emphasizing certain text from the user and causes text to be automatically emphasized.

For example, WIPO Patent Application Publication WO 2012/094725 describes a system that takes biometric readings of the text message sender, and then modifies the appearance of the text message to reflect the biological response al state of the text message sender. For example, if the text message sender is highly agitated, then the font and/or size of text may be enlarged, jagged, bolded, etc. However, like emoticons, font changes may or may not clearly convey the biological response of the text message. For example, the font style "bold" may convey excitement, anger, fear, a feeling of being hurried, etc., which are different, if not incompatible, biological responses.

Thus, in this case the related art, either singularly or in combination, fails to provide devices or a system that clearly represents the biological response of a sender of a text message. Furthermore, the art fails to provide a system that conveys the biological response of a recipient and/or participant of the event. The present disclosure provides one or more solutions to this long-felt need.

Definitions

For the present disclosure the following terms are defined for the purposes of understanding throughout the specification.

Ephemeral which is defined as the ability to provide a temporary period of time and ephemerality is the ability to implement an ephemeral basis for transactions, events, recorded and otherwise.

Securitization which is defined as by using encryption by implementing public/private as well as symmetric/asymmetric as well as shared polynomial keys. Non-encryption includes multifactor authentication, hashes, single and multi-sign on ephemeral pins and just plain personal identification numbers, named passwords, biometrics, certificates, etc. This includes industry standard encryption methods for any of the terms included herein.

Monetization here is defined as the ability to receive payments as compensation in the form of salaries from employment as well as from services and products. This includes digital currency digital tokens, cash, checks wire transfers ACHs (automated clearing house), notes, mortgages, royalties, dividends, and includes transactions that may or may not require swapping, bartering, and/or asset swaps.

Guaranteed herein is defined in the usual dictionary terminology in that a guarantee provides certainty and/or is a product/process/service that is approved and assured.

Warrantied here describes a process/product/service where a guarantee can be provided that a certain outcome or obligation will be fulfilled regarding that process/product/service.

Constraints herein are defined as time limited electronic transactions that include geolocations, and constrained devices which are time limited.

SUMMARY

According to an embodiment of the present invention, devices are utilized to represent biological changes of a participant and/or spectator of an event which is captured in an electronic data event session.

More specifically, the present disclosure describes one or more devices comprising at least one computer processor that acquires and processes human biological change data from event data steam(s) that allows for ranking one or more changes in the biological change data and correlates the biological change data with ranking statistics from an event and wherein the correlation identifies and measures a magnitude of change of the human biological responses from data acquired from the event data stream(s) so that correlation of the biological change data with the ranking statistics creates one or more objects for storage and analysis within in one or more databases, wherein the objects possess time synchronized temporal human biological responses before, during, or after an event and wherein the objects also possess biological change data that utilizes correlation of the biological change data with the ranking statistics and results in objects that also contain one or more ranked values of the human biological responses.

Rankings of the human biological responses can be based upon changes in emotional highs and lows based on facial and body postures, biophysical reactions including heartbeat, blood pressure, and any other physiological-related measurable changes. Rankings scales can utilize any numerical and/or statistical methodology known and/or already in use.

Here the objects may be tangible, real, physical objects and/or objects that are intangible and/or virtual objects.

In addition, the objects can be cryptographically secured, assigned ownership, and sealed such that an ownership record is generated.

An ownership record of the data can be stored in an irrevocable database.

In an additional embodiment, the devices comprise a correlator/decider portion that includes one or more devices that triggers the rankings such that a content value is generated and wherein the rankings correlate with a change in sign, and magnitude of the human biological changes are determined and wherein the correlation provides a value of at least one segment of the event stream.

The ranking statistics of an event stream utilizes game rules with multiple human referees and judges during a multitude of time synchronized human biological responses during said event data stream.

The value of a segment of an event data stream triggers generation of a contract for ownership of a determined valuable segment of said event data stream, an actual event, or attributes of an event wherein said event data stream(s) identifies, captures, quantifies, ascertains, analyzes, and packages human biological reaction data.

These devices can exist in or within an intranet, internet, or cloud data handling system so that the devices can function in conjunction with computers that have access to computer networks.

The biological state can be captured instantaneously or after an event that influences and/or causes the biological state and wherein the biological state includes a biological response state of existence and wherein the biological state is temporal in that past and present data is available for collection and analysis and eventual prediction of future biological states at any time by a user of the one or more devices.

The devices and objects maybe selected from at least one of a group consisting of smart phones, video and/or digital cameras, tickets, and tokens.

Individuals can share at least one of a group consisting of a common grouping, location, language and understanding of an event or events that is observed and/or within which the individuals are participating.

As input data is collected via a data collection funnel the funnel can function as a device that collects data which includes associated time stamps and geo location features.

In addition, data flows along a directed flow path toward a Big Data Cluster device that accepts and associates data and data streams via a data associator, organizes via a data organizer, and stores data in a database and wherein the Big Data Cluster device includes a database which contains data content provided in audio, video and/or audio/visual and textural data over a specified time interval.

The Big Data Cluster device includes a time ordered time interval and wherein said Big Data Cluster device includes a data organizer that associates data with a data associator.

The data associator includes all data from all points of origin creates multiple tracks of data for each of any original source data inputs that reside in the Big Data Cluster such that a locater provides a location and address for the data inputs to reside.

The data source inputs within the locater provides complete available information regarding location, perspective viewing angles, distances and recording instruments of events so that the data sources are now also organized and located in data tracks.

Each data track is streamed data that includes at least geolocations, movement, angles, and recording capabilities of one or more events so that data tracks themselves can be further analyzed.

An aligner provides time synchronization of and for various events captured as data streams wherein the aligner gives preferential integrity to the data streams and wherein in addition the aligner adjusts for geolocation and recording delays associated with each data stream at a specific geolocation.

The aligner also produces a time synchronizer that provides instantaneous time along each input data stream.

An identifier/quantifier is utilized as an intelligent comparator processor that leverages data in the Big Data Cluster to determine data points of interest that occur at any time associated with the events.

As data and data streams are created, collected, and organized, an intelligent comparator processor with an intelligent comparator identifier and an intelligent comparator quantifier is employed so that the data and data streams can be utilized and provided as storage vectors of time with synchronized tensors of expressed precursors of a quantifiable change in biological reactions, wherein the tensors are a data structure used in linear algebra that may include vectors and matrices allow for calculation of arithmetic operations with the tensors wherein the tensors are also a generalization of matrices represented using n-dimensional arrays.

Data is further processed with a biological comprehender/editor that allows for analysis of one or more sentiment intensities during specific times and/or time intervals during said event and sums all said data and data streams in columns biological responses that can be summed and tabulated at any instant in time or time interval to produce a consistent record of any biological intensity that occurs across an entire event.

The comprehender/editor also provides a scale that yields a biological score from an elevated positive value to a lower ranking negative value such that values and associated ranks are assigned based upon biological reactions of one or more individuals in relation to themselves and each of other individuals.

The production of biological intensity values is tracked, captured and is ultimately editable by an editor portion of the comprehender/editor to provide an adjustable output of an edited version of raw biological change intensity data along associated data tracks.

In addition, a predictor is included that provides a neural network and artificial intelligence iterator and algorithm predictions that utilize an entire data set ultimately obtained from an adjustable output of edited versions of the raw biological change intensity data along data tracks.

Here, the predictor predicts biological states by inputting data into its neural network and wherein the predictor trains and retrains itself by utilizing continuous data processing feedback loops to produce outputs that match the edited versions of raw biological change data intensity along data tracks and wherein the feedback loops iterate until predicted results match manually edited results.

The training and retraining is data that is captured in a memory of the predictor and every time a new data set is accessed, utilized, organized, and analyzed within or external to the one or more databases iteration of the data along data streams reaches a more precise satisfactory representation of actual biological response(s).

Finally, a packager is included as a portion of the devices that extracts data from one or more data sets wherein the data is contained in the data sets as data slices and/or other subsets of data that are optionally contained in the objects and that allow for selectivity of the data sets according to desired types and intensities of one or more biological changes of magnitude measured by the devices.

The objects can be selected from any one or more of a group consisting of fungible tokens, non-fungible tokens, CDs, DVDs, memory storage devices, records, and printed tickets.

In another embodiment, an electronic data event session monitoring device intercepts a current event using electronic data event sessions. The current event data is generated by an initial sender, and the current event data is addressed to an addressee. The electronic event session monitoring device receives a current photo of the initial sender of the current event session, where the current photo is taken contemporaneously with a generation of the current event session by the initial sender. The electronic event session monitoring device, based on at least one previous photo taken of the initial sender while generating a past set of data involving other electronic event data in the same or similar contextual content as the current event, determines whether the current photo accurately represents a state of mind of the initial sender while generating the current message. It is possible to determine that the current photo accurately represents the biological response change of the initial sender when generating the current change in response of the electronic response data session monitoring device that transmits both the current event data and the current photo of the initial sender to the addressee.

In an embodiment of the present disclosure the electronic event session monitoring device, in response to determining that the current photo does not accurately represent the biological change of the initial sender when generating the current event data, transmits both the current event data and at least one previous photo of the initial sender to the addressee.

In a further embodiment of the present disclosure the electronic event session monitoring device receives biometric sensor readings of the initial sender from one or more biometric sensors coupled to the initial sender. The biometric sensor readings are taken while the initial sender is generating the current message. Based on the biometric sensor readings, the electronic event session monitoring device determines whether the current photo accurately represents the biological change and associated state of mind of the initial sender while generating the current electronic event data set.

In an embodiment of the present invention, the current event capture is sent from a communication device that supports the electronic event session, and the communication device has a geophysical location sensor. The electronic event session monitoring device determines a geophysical location of the communication device while the initial sender is generating the current event data, and then further determines the biological response of the initial sender while generating the data based on the geophysical location of the initial sender while generating the current event data.

In an embodiment of the present disclosure, a computer program product represents a biological response of a participant in an electronic event session. The computer program product comprises a computer readable storage medium having program code embodied therewith, and the computer readable storage medium is not a transitory signal per se. The program code is readable and executable by a processor to perform a method that includes, but is not limited to: intercepting current event data from an electronic event session, where the current data is generated by an initial sender, and where the current event data is addressed to an addressee; receiving a current photo of the initial sender of the current event data, where the current photo is taken contemporaneously with a generation of the current event data by the initial sender; determining, based on at least one previous photo taken of the initial sender while generating past event data message having a same contextual content as the current event data, whether the current photo accurately represents a state of mind of the initial sender while generating the current event data; and in response to determining that the current photo accurately represents the state of mind of the initial sender when generating the current data, transmitting both current data messages and the current photo of the initial sender to the addressee.

The presently disclosed devices and associated system thus provides a technological advantage over the prior art, in that it improves the efficiency and accuracy of conveying the state of mind of senders and/or recipients of event data. More specifically, without the teachings of the present disclosure, many, if not most, event data capture and analysis would be ambiguous, and thus subject to misinterpretation.

BRIEF DESCRIPTION

DETAILED DESCRIPTION

Figure 1:
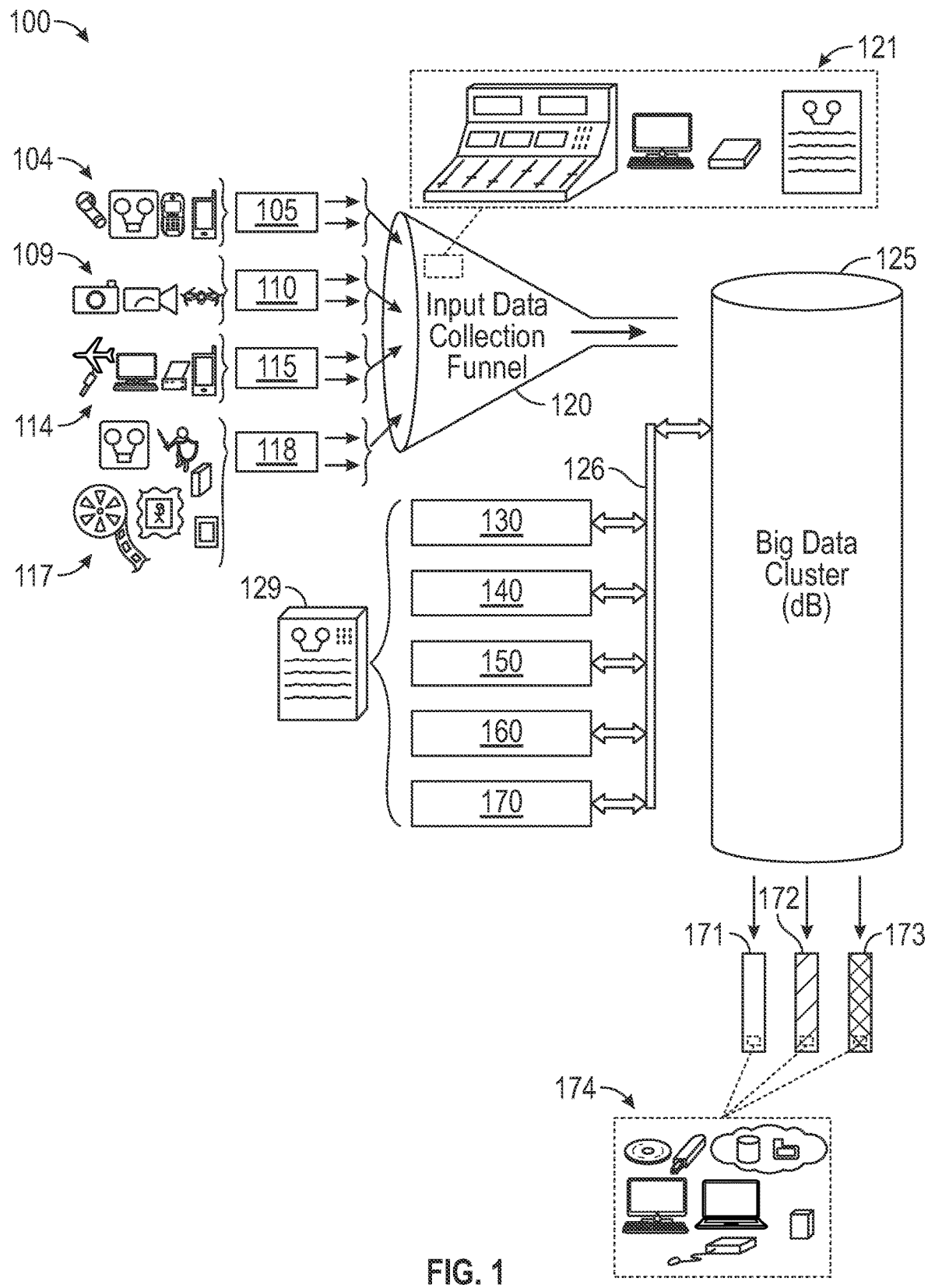
FIG. 1 is a schematic representation of one or more devices and associated processes that collect, measure, quantify, compare, capture, and package changes in human biological content using existing hardware/software interface technologies to accomplish these tasks.

FIG. 1, (100), represents the overall device that identifies, extracts, and analyzes the human based biological reaction data that includes biological responses and physical responses, and securely packages selected biological reaction data and the context of the biological reaction data Here, (105), (110), (115) are audio, video (and/or audio/visual [105/110] and textural data which can be augmented from additional sources with data inputs. This includes news feeds, social media feeds, etc., either in real time or with various time delays. Item (118) is a meta data source which includes ranking statistics from an event, historical records, photos, films, phrases, books, from data libraries which include additional contextual meaningful information and more that adds richness to the data set. The data is collected via a data processor such as a computer and/or computer network that exists as an intranet, internet, or cloud computing device capable of accessing, processing, and storing the data as it is collected. Devices for this purpose include the use of microphones, tape recorders, cell and smart phones (104) which provide data collected by the audio data inputs (105). Additional devices (109) include cameras, video/moving cameras and (114) which are airplanes and drones with and without cameras, computers, fax machines/scanners and printers, and two-way communication devices that provide data collected by textural data inputs (115). These devices (105, 110, 115) can all transceive data including optical images from such real items as tape recorders, statues, books, paintings, reels of film, and even baseball cards (117). The data may be maintained in the data processor and extracted as needed to provide the necessary cumulative and iterative information with the ability to accurately and precisely ascertain the biological state and state of mind of an individual or groups of individuals. The meta data source (118) includes ranking statistics from most any event, historical record, photo, film, phrases, as well as books from data libraries which include additional contextual meaningful information and more that adds richness to the data set. The data is collected via a data processor such as a computer and/or computer network that exists as an intranet, internet, or cloud computing device capable of accessing, processing, and storing the data as it is collected. These individuals may or may not have a common grouping or location or language or even understanding of the event or events they are observing and/or within which they are participating.

Item (120) is an input data collection funnel that collects/gathers data (105,110,115,118) and provides their associated time stamps, geo locations, and additional features so the equipment can collect the data. The data can be collected with several different devices (121) such as audio/visual data mixers, desktops and other lap top computers, data acquisition devices (DAQs), and larger computer devices as shown. The data path then flows to the Big Data Cluster (125) (database) dB. This Big Data Cluster dB (125) is one or more databases which contain the entire content(s) of (105), (110), (115), audio, video (and/or audio/visual [105/110] and textural data as data tracks (127), along with 118 (meta data sources), over a desired time interval and optionally over a time ordered interval. The Big Data Cluster dB (125) connects bi-directionally with all processing units (130, 140, 150 160, 170) using one or more Communications Channels (126) that can be one-way but are normally two-way Communications Channels.

A main frame or other large computing device (129) (large in terms of data memory and fast data processing speeds) provides for a data organizer (130) for the Big Data Cluster dB (125) as well as (140) which is an intelligent comparator for the Big Data Cluster dB (125).

Next, the data is further processed with a biological comprehender/editor (150) that allows for the analysis of various biological intensities correlated with ranking statistics during specific times and/or time intervals during the event—so that the biological comprehender/editor (150) processes all the data in columns so that it can sum the changes in biological responses including state of mind biological responses at any instant in time or time interval and produces a concise and consistent record of the biological intensity of those responses correlated with ranking statistics extracted from metadata (118) across the entire event. This includes all categories of the biological changes and/or changes in the state of mind. A predictor (160) is included, which includes a neural network with artificial intelligence iterators and prediction algorithms that utilize the entire data set. The predictor (160) predicts by inputting data which includes a neural network and is trained to produce the output to match the edited version from the Biological Comprehender Editor (150). The packager (170) is the portion of the device that extracts each edited version from the Biological Comprehender/Editor (160) as data from the Big Data Cluster (125) and securely stores the data in data slices (171) or other data subsets (172, 173).

Figure 2:
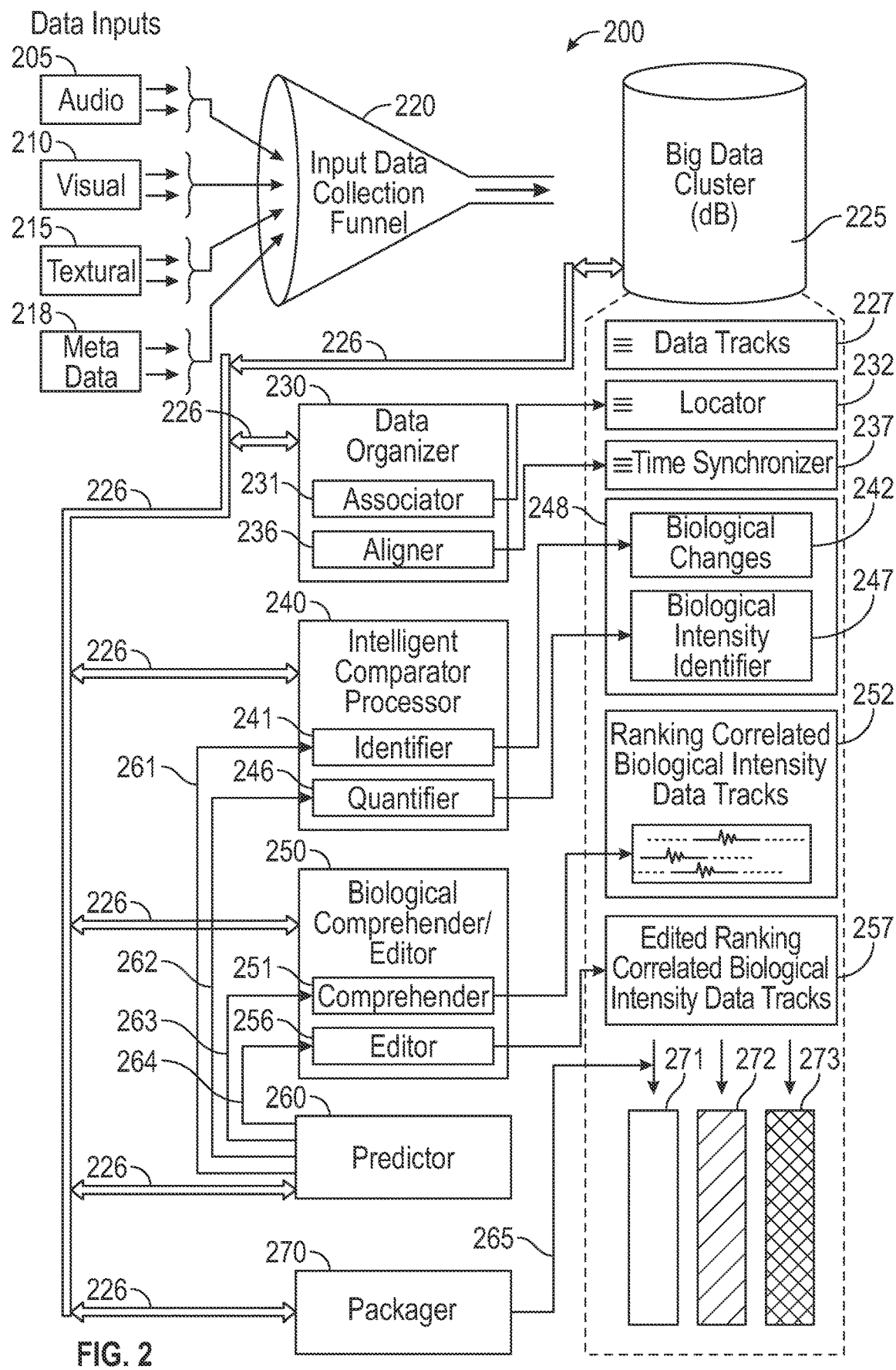
FIG. 2 is a schematic representation of devices and associated process(es) that collect, measure, quantify, compare, capture and package changes in human biological content as data that is acquired and organized in various databases and utilized to provide tokens representative of the data.

FIG. 2, (200) represents the overall device that identifies, extracts, and analyzes the human based biological reaction data that includes biological response and physical responses.

Here, (205), (210), (215) are audio, video (and/or audio/visual (205/210)) and textural data which can be augmented from additional sources with data inputs. This includes news feeds, social media feeds, etc., either in real time or with various time delays. Item (218) is a meta data source which includes ranking statistics from an event, historical records, photos, films, phrases, books, from data libraries which include additional contextual meaningful information and more that adds richness to the data set. The data is collected via a data processor such as a computer and/or computer network that exists as an intranet, internet, or cloud computing device capable of accessing, processing, and storing the data as it is collected. The data may be maintained in the data processor and extracted as needed to provide the necessary cumulative and iterative information with the ability to accurately and precisely ascertain the biological state and state of mind of an individual or groups of individuals. These individuals may or may not have a common grouping or location or language or even understanding of the event or events they are observing and/or within which they are participating.

Item (220) is an input data collection funnel that collects/gathers data (205, 210, 215, 218) and provides their associated time stamps, geo locations, and additional features so the equipment can collect the data. The data path then flows to the Big Data Cluster dB (225) (database). This Big Data Cluster dB (225) comprises one or more databases which contain the entire content(s) of (205), (210), (215), audio, video (and/or audio/visual [205/210] and textural data (215) that exist or are stored as data tracks (227), along with 218 (meta data sources), over a desired time interval and optionally over a time ordered interval. The Big Data Cluster dB (225) connects bi-directionally with all processing units (230, 240, 250 260, 270) using one or more Communications Channels (226) that can be one-way but are normally two-way Communications Channels.

Item (230) is a data organizer for the Big Data Cluster dB (225). First the data organizer [230] associates with the Associator (231) for all the data tracks (227), for all the points of origin of the data, the complete associated location information as a locater (232) The data organizer (230) creates tensors in the big data cluster to formally organize the data into multiple tracks of data. This locater (232) provides complete available information which describes and quantifies the location as well as providing the location perspective viewing angles, distances, and the capabilities of the recording instruments. Data tracks (227) are streamed data that includes for example geolocations, movements, angles, and recording capabilities, so that the data tracks (227) themselves can be further analyzed together using the locator (232) information, to process the data tracks (227) from multiple vantage points. Next the Aligner (236) provides time synchronization (see [237]) of the various event streams that gives preferential integrity to the streams. In addition, the aligner (236) adjusts for the geolocation and the recording delays associated with each data stream at a specific geolocation. The Aligner (236) produces a time synchronizer (237) that provides the instantaneous time for each of the input data streams.

Item (240) is an intelligent comparator for the Big Data Cluster dB (225), which has an Identifier (241) portion and a Quantifier (246) portion that process data in the Big Data Cluster dB (225), to determine temporal intervals that include biological intensities quantified by biological data sentiment associated with the event. As the data and data streams are created, collected, and organized, the intelligent comparator (240) is employed so that the data from Big Data Cluster dB (225), the locator (232), and the time synchronizer (237) can be utilized for storage tensors of time which are synchronized tensors of expressed precursors of biological responses in a tensor storage unit (248) that includes the biological changes and biological intensity identifier. These expressed precursors of biological responses in the tensor storage unit (248) are developed and processed in two steps. Normally, for the first step, the identifier (241) is comprised of mathematical comparator algorithms that allow for mathematical comparisons which identify the biological changes (242) which is a data set of biological responses. The second step requires/utilizes the data from Big Data Cluster dB (225), the locator (232), the time synchronizer (237), and the biological changes (242), to quantify biological responses via the quantifier (246), which mathematically identifies and quantifies dynamic extraction data that creates the biological intensity identifier (247) which includes the audio (205) and video (210), audio/video (215) and other metadata sets (218) as also shown and described in FIG. 1.

Next, the data is further processed with a biological comprehender/editor (250) that allows for the analysis of various biological intensities correlated with ranking statistics during specific times and/or time intervals during the event—so that the biological comprehender/editor (250) processes all the data in columns so that it can calculate (using neural network algorithms) the changes in biological responses including state of mind biological responses at any instant in time or time interval and produces a concise and consistent record of the biological intensity of those responses correlated with ranking statistics extracted from metadata (218) across the entire event. This includes all categories of the biological changes and/or changes in the state of mind. This involves a stepwise process that includes the comprehender portion (251) of the biological comprehender/editor (250) which produces the ranking correlated biological intensity data tracks (252) that exist in the Big Data Cluster dB (225) and also provides a scale that yields a biological ranking from an elevated positive value to a lower ranking negative value. These values are assigned in a relative fashion based upon the biological reactions of one or more individuals. The production of the ranking correlated biological intensity data tracks (252) is captured and now editable by the editor portion (256) of the biological comprehender editor (250). This leads to an adjustable output of the edited ranking correlated biological intensity data tracks (257) from the editor portion (256) and comprehender portion (251) of the ranking correlated biological intensity data tracks (252).

A predictor (260) is included, which includes a neural network with artificial intelligence iterators and prediction algorithms that utilize the entire data set, which is ultimately obtained from an adjustable output of the edited ranking correlated biological intensity data tracks (257) of the comprehender portion (251) of the ranking correlated biological intensity data tracks (252). This includes data that is stored, analyzed, and/or retrieved from the Big Data Cluster dB (225), the locator (232), the time synchronizer (237), the tensor storage unit (248) with the biological changes (242) as well as the biological intensity identifier (247), the ranking correlated biological intensity data tracks (252), and as stated above, the edited version of the edited ranking correlated biological intensity data tracks (257) of the editor portion (256) of the biological comprehender/editor (250).

The predictor (260) predicts by inputting data which includes a neural network and is trained to produce the output to match the edited version from the product of the edited ranking correlated biological intensity data tracks (257) processed from the editor portion (256) of the biological comprehender editor (250). The process of training the neural network provides data feedback loops (261, 262, 263, and 264) which retrain the algorithms. Specifically, (261) retrains (241) which is the identifier portion of the Intelligent Comparator Processor (240), (262) retrains (246) which is the quantifier portion of the Intelligent Comparator Processor (240), (263) retrains (251) which is the comprehender portion of the Biological Comprehender Editor (250) and, (264) retrains (256) which is the editor portion of the biological comprehender/editor (250). These feedback loops (261,262, 263, and 264) and predictor (260) continue to iterate until the predicted results match the manually edited results which are contained in edited ranking correlated biological intensity data tracks (257). This training process is captured in the memory of the predictor (260) and every time a new data set is accessed, utilized, organized, and analyzed, the iterative process reaches a more precise satisfactory representation of the actual biological response(s).

The packager (270) is the portion of the device that extracts data from the Big Data Cluster dB (225) in data slices (271) or other data subsets (272, 273) that allows for selectivity according to the desired types and intensities of biological changes, including biological responses as defined by the edited ranking correlated biological intensity data tracks (257) of the editor portion of the biological comprehender/editor (250). The Packager (270) through the Export Communication Bus (265), can also directly provide the output of three datasets (items 271, 272, 273).

The packager (270) provides the ability to securitize (in any combination of temporally, geographically, personally, corporately, hierarchically, specifically, directly, indirectly, numerically, and logically), and to provide this information as NFTs (non-fungible tokens) or some other form of virtual or real tokens that provide the user of the tokens to use the captured data provided by this device.

Figure 3:
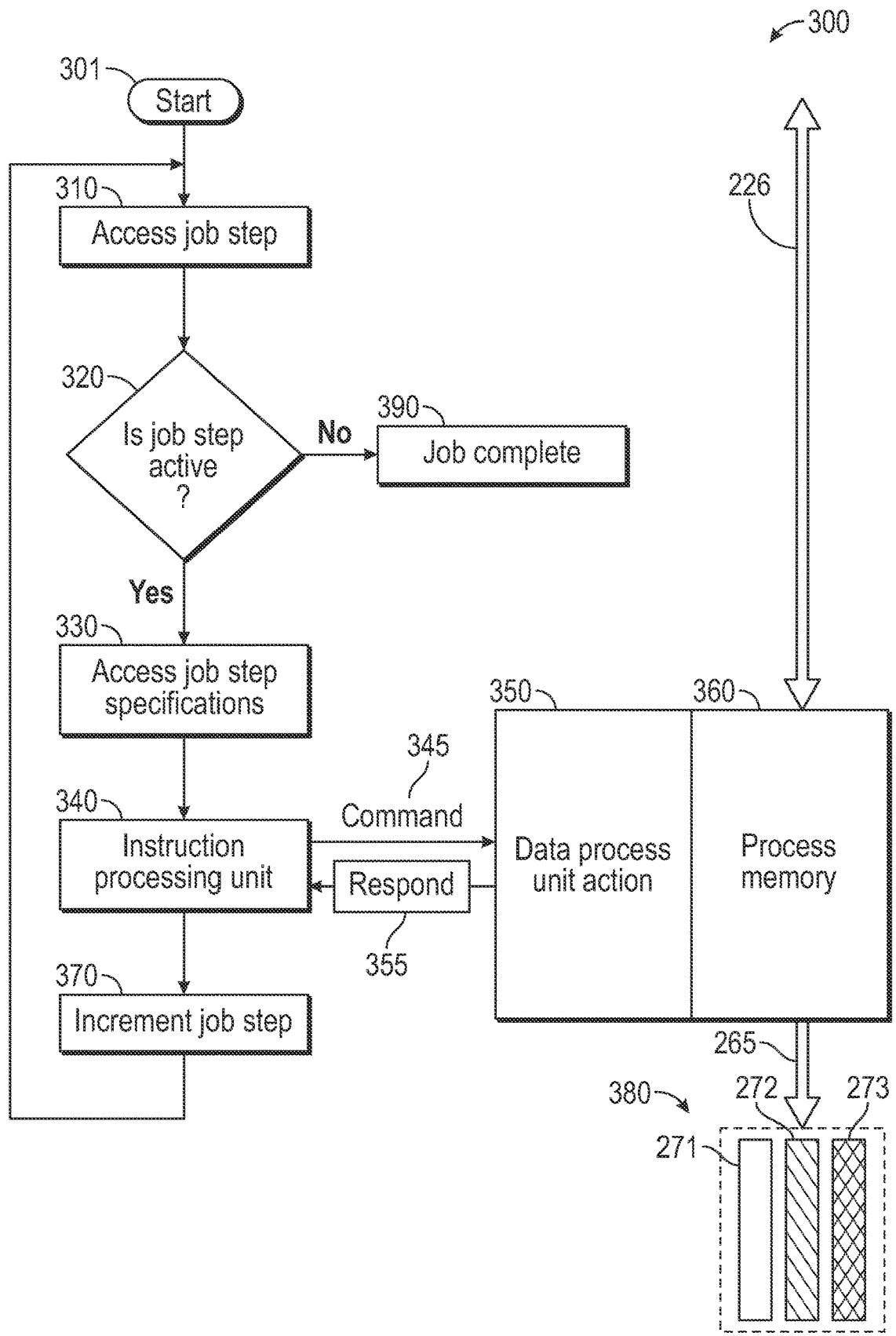
FIG. 3 is a schematic representation of the Packager Process with a data flow chart.

FIG. 3, (300) provides a schematic representation of the Packager Process as well as a flow chart that indicates how the process proceeds. Initially, (301) is the START of the Packager Job Instruction Process. The Packager is given a job in the form of data that consists of Job Instruction steps. Each Job Instruction Step contains Specifications to be carried out by the Packager according to this Job Instruction Step. Conceptually, this portion of the process is similar to the IBM JCL (Job Control Language).

Here (310) is a locater that represents the location and device (real or virtual device) where Access is provided for the Job Instruction Step. The decisions are provided at (320), a determiner which determines if there is an active Job Instruction Step. If there is no active Job Instruction Step (NO branch), the Job is completed as shown in (390), the Job Log is saved, and the Packager (270) exits to await another Job.

In addition, at (320) the determiner (320), allows for a decision to be made to determine if there is an active Job Instruction Step. If there is an active Job Instruction Step (YES branch), the Job continues to (330), the accessor (330) which accesses the current Job Instruction Step Specifications. The Specifications can be as simple as WAIT for (a Human or other machine made) Response, to complex logic that acts iteratively upon the entire Dataset.

The Job Instruction and Specifications are sent to an Instruction Processing Unit (IPU), (340) that interprets the Instruction and Specifications by utilizing a series of Commands (345) to the Data Process Unit (350). The Data Process Unit (350) provides computational ability that provides accelerated Import, Database, Vector, Tensor, Securitization, Monetization, and Export operations. These capabilities are necessary for fast and efficient operation for processing the large datasets which the Packager must handle. Data Process Unit (350) processes each Command (345) and returns a Response (355) to the Responder (355) to the Instruction Processing Unit (340). The Data Process Unit (350) is supported by at least one or more dedicated Process Memory(s) (360). This Process Memory, (360) is connected to Communication Channels (226 as shown in FIG. 2) for direct access to all the data and functionality of the entire device (200 of FIG. 2).

This Process Memory (360) is also connected directly to the Packager Export Unit (380) through at least one Export Communications Bus (265). The Packager Export Unit (380) is herewithin depicted as outputting three datasets (items 271, 272, 273 of FIG. 2).

When the Instruction Processing Unit (340) has completed the current Job Instruction Step and all of the Specifications, the Packager Process Flow, as shown, continues to Increment the Job step (370) using the Incrementor (370) and provides a feedback loop back to the Accessor (330) to begin and/or include another Job Step.

A specific example is herewith provided as follows;

The first job instruction step Imports a dataset from the Big Data Cluster dB (225). The Specifications could be to Import only the single most emotionally ranked one-minute intervals of the mission. The Packager Job Instruction Process then processes as follows: The Packager (270) is given a job, consisting of Job Instruction steps. The Packager Job Instruction Process is entered at START (301). Accessor (330) utilizes Job Step (310) and finds the first Job instruction step, proceeding to (320), the determiner which decides if there is an active Job Instruction Step. Here the Accessor (330) accesses the current Job Instruction Step Specifications, so that the Instruction Processing Unit (340) can receive the Job Instruction and Specification. The instruction is to Import a dataset from the Big Data Cluster dB (225) with Specifications that include only the single most emotionally ranked one minute interval of the mission.

The Instruction Processing Unit (340) issues a Command (345) to the Data Process Unit (350) to Clear the process memory (360). When this task is complete, a task complete response is generated by the Data Process Unit (350) via the Responder (355) to the Instruction Processing Unit (340). The Instruction Processing Unit (340) issues a second Command (345) to the Data Process Unit (350) to Import a dataset from the Big Data Cluster dB (225) using one or more Communications Bus(es) (226), specifically utilizing a dataset located in the Edited Ranking Correlated Biological Intensity Data Tracks (257), matching a criteria of the single most emotionally ranked one minute interval of the mission. When this task is complete, a task complete response is generated by the Data Process Unit (350) via the Responder (355) to the Instruction Processing Unit (340). In this manner, the Instruction Processing Unit (340) has completed the current Job Instruction step and all the Specifications. The Packager Process Flow, as shown, continues to Increment the Job step (370) and loop back to the Accessor (330) to operate on another Job Step.

To monetize these devices and systems, it is possible to acquire desirable packaged data in specific time intervals so that any individual(s), organization, or other entity can purchase the time intervals that allows for viewing the desirable packaged data upon request. These desirable packaged data can be captured real or virtual and include events, sports, historical, and other private and public memorabilia, collections of coins, minted paper, stamps, rooms and offices in homes and businesses, etc. Purchase of the packaged data in specific time intervals can be sold as tokens and/or stored data retrieved from any of the devices described above.

One example of creating, packaging, protecting and monetizing the devices and systems that measure, quantify, compare, package, and capture human content in databases is as follows:

In one embodiment, the event being processed by the device is the first human Lunar landing by NASA, using the Apollo 11 spacecraft on Jul. 16, 1969. The application of the device is demonstrated below in order to further understand the concept and magnitude of this disclosure.

Audio data was obtained by microphones and stored on tape recorders. Visual data was on film with photographic cameras. Some was scanned and then stored in various digital forms. Video data was obtained with video cameras of many varieties, including on the spacecraft itself, and recorded to video tape. Textural data was produced in abundance by millions of people around the world in many forms, including newsprint, saved on microfilm, and later scanned into digital data. A plethora of meta data of this event exists in archives, museums, exhibits, interviews, and so on. These data sources are fed into the input data collection funnel devices and become the Big Data Cluster, with some subset of this data being in temporal sequences as data tracks.

The Big data cluster dB is then processed using the Data Organizer device, a purpose built mainframe computer designed to Associate and Align the data tracks. The Associator finds and adds location information to the data tracks. As this event is geographically diverse, including the entire Earth and Moon, there is much location information to add. The Associator gathers and tags each data track to the best resolution obtainable. Next the Aligner creates a Time Synchronizer which references each data track back to some specific time reference point, e.g. Greenwich Mean Time. This requires dynamically sliding the time reference during each data track to take into account the rotation of the Earth, radio transmission delays in some tracks from other places on Earth and the Moon, relay station delays, such as the radio hop from the Lunar surface, to the orbiting space vehicle, then to Earth, and through various land and radio links. The result is all data tracks become Time Synchronized to one single time reference point.

Now another purpose-built mainframe computer processes the Time Synchronized data tracks with the Intelligent Comparator Processor. This Processor uses initial algorithms which are modified and tuned via neural network feedback loops, to Identify and Quantify the data tracks for Biological Changes and Biological Intensity. In this case, most of the biological change data is inferred by body posture, movement, facial feature changes, audio amplitudes, frequencies, and dynamics. There are some unique data tracks available for this event because the Astronauts have biological sensors to provide real-time monitor bodily functions. The result is data tracks from around the world, time synchronized to the event on the Lunar surface, which rank the specific biological intensity of millions of people around the world.

Next, the Biological Comprehender Editor, another purpose-built mainframe computer, utilizes initial algorithms which are modified and tuned via neural network feedback loops, to produce the Ranking Correlated Biological Intensity Data Tracks. This device finds correlations between human biological intensity and various ranking features within the meta data. One case is easily understood to almost all humans, that is the moment Captain Neil Armstrong steps on the lunar surface and says, "That's one small step for a man, one giant leap for mankind." The following is one example of a possible series of actions that the Comprehender utilizes to locate and identify this particular event to so that a high ranking of meta data being correlated with biological intensity:

1) Meta data of the flight timeline is correlated with the biological intensity of millions of human biological data track in the Biological Intensity Identifier. Note that these have already been time synchronized to account for the Earth and Moon to Earth delays.

2) A strong correlation is found at the flight time of the first step on the lunar surface. That provides of extreme biological intensity which are found to be time synchronized with a specific flight time event.

3) Meta data is further analyzed so that large numbers of meta data items are found which refer to this specific event. This indicates a broad impact of human biological intensity had lasting effects which further increases the correlation.

4) Meta data analysis finds photos, quotes, books, films, etc. which also references this same event.

5) Historical records and displays exist for multiple museums all over the Earth are provided and located in the Meta data, further strengthening the correlation.

6) All of the data items are tagged as correlating to the event with specificity to the linkage of each item which strengthens (or weakens) the correlation. These tags essentially are pointers to all the contributing data for this event, and now comprise a virtual data set of the event as it resides in the Big Data Cluster dB.

The Editor device is now utilized by human operators to review the output of the Comprehender device. The Editor allows easy and fluid access to the Ranking Correlated Biological Intensity Data Tracks. These capacities and capabilities mirror that of a multi-track audio-visual editing studio that also includes meta data immediate access, virtual 3D gear with multi-person full immersion and interactive editing controls. This allows an editing team to quickly review the data sets with a multiplicity of editing controls.

The results of the editing team are provided as the Edited Ranking Correlated Biological Intensity Data Tracks. In this example for instance, the Editor can be used to trim the first step on the Moon event to only include one minute of responses from the actual event. This would trim out all of the writing, articles, and reporting, leaving simply the "instantaneous" euphoric world-wide human biological response and the one minute of photos and video of the event itself.

Next the Predictor device is used as required or desired to update the training of the neural networks in the Intelligent Comparator Processor and the Biological Comprehender/Editor. The Predictor device is a neural network training device with the requisite logic and memory capabilities to update and control the neural networks of the Intelligent Comparator Processor and the Biological Comprehender/Editor. The Predictor has the forward driving capabilities to iteratively rerun these devices while tuning the neural networks and driving toward convergence with the human decisions resulting from the Editing process. The Predictor also has the memory to record each iteration to "undo" the neural network tuning to remove poor decision branches.

In this example for instance, the Predictor would only be allowed one iteration of neural network training since the event is very unique and many years in the past.

The Packager device is another purpose-built mainframe computer. The Packager allows limited external viewing of data slices and data sets which are identified in the Edited Ranking Correlated Biological Intensity Data Tracks, and exist in the Big Data Cluster dB. If it is desirable to package some data slice or data set (or some sub-set), the Packager device is utilized.

The Packager device exports the desired data from the Big Data Cluster dB, and securitizes this data as specified in the export specifications (curated). The data could be curated for a wide variety of uses, and with a wide variety of restrictions for use, such as:

1. Public Records, Open Source, Open Documents, Free Documents commons.

2. Copyrighted, trade-marked, water marked materials.

3. Tokenized materials (including Non-Fungible Tokens) with or without securitization and use limitations.

The Packager device keeps records of each data export and the specified limitations of the use of the data. In some cases, the data export may be fully released into public space with no limitations. In other cases, there may be very tight limitations on the data export which may utilize securitization (in any combination with temporal, geographical, personal, corporate, hierarchical, specific, direct, indirect, numerical and/or logical data analysis). The enforcement of the securitization is possible by utilizing the Packager device itself, or enforcement could be entirely exported to some other devices.

In this example for instance, if the Editor was used to trim the first step on the Moon event to include only one minute of responses from the actual event, this would trim out all of the writing, articles, and reporting, leaving simply the "instantaneous" euphoric world-wide human biological response and the one minute of photos and video of the event itself. The Packager may be used to simply package the millions of human one-minute responses into some public record with no securitization. Alternately, the Packager may be used to group some subset of the data as some artistic photo and/or audio mosaic with strong securitization of the viewing and distribution of this artistic work. Since an artwork has been curated from the data set in a unique way, there may be a multiplicity of monetizing components which are attached to the artwork. These securitization and monetizing functions may be left to reside in the Packager device itself, or exported to some other device. Parsing this data to provide for multiple data sets, all of which can be sold for some value to individuals and/or organizations is another goal of the present disclosure.

More specifically in this case, the packager (270) provides the ability to securitize (in any combination) temporal, geographical, and personal biometric attributes, as well as any group of real or virtual construct of a living or non-living entity. This includes a corpus that also provides an ability to construct a hierarchal identification with some degree of specificity such as a genome sequencer or other biological identifier and providing the capability to refer either directly or indirectly to one or more objects. This is performed digitally using numerical techniques to provide a list or formula and with logic for performing a decision during the process. This information is then provided to the NFTs (non-fungible tokens) or some other form of virtual or real tokens that provide the user of the tokens with the ability to use the captured data provided by the Packager.

The Packager device is a device that packages digital and/or analog content including photos videos audio and audio/visual files from one or more data funnels. It performs this function by moving and where necessary manipulating the data into a dynamic digital marketplace/space. In turn this allows for financial constraints and/or for bidding to complete any and all financial transactions which are not limited to but include digital transactions.

In this example for instance, if the Editor is used to trim the data for editing the first step on the Moon event to include only one minute of responses from the actual event, the Editor's function is to trim/edit out all of the writings, articles, and reports, leaving simply the "instantaneous" (and likely euphoric) world-wide human biological response and the one minute of photos and video of the event itself. The Packager, in this case, is used to simply package the millions of human one-minute responses into one or more public records without securitization. Alternately, the Packager can be used to group some subset of the data as some artistic photo and/or audio mosaic with strong securitization of the viewing and distribution of this artistic work. Since an artwork has been curated from the data set in a unique way, there are a multiplicity of monetizing components which are attached to the artwork. These securitization and monetizing functions are left to reside in the Packager device itself. It is also possible that these functions can be exported to other devices. Parsing this data to provide for multiple data sets, all of which can be sold for some value to individuals and/or organizations is another goal of the present disclosure.

A working example of Packaging the first step on the Moon event is the release of a public archive to the general public of the single most emotionally ranked one minute interval of the mission. The Packager device is utilized to extract the dataset, convert the content to a publicly available open-source formats, and export the data in a single data file placed into a freely available and accessible public data archive. The Packager is given job instructions to accomplish this set of tasks. The job instructions contain the step-by-step operations to be performed and the specifications for each job step.

The first job instruction step is to Import the single most emotionally ranked one minute interval of the mission. The Packager accesses the Big Data Cluster dB and Imports the Edited Ranking Correlated Biological Intensity Data Tracks that meet the job specifications for this job step. In this case the specifications are "Import only the single most emotionally ranked one minute interval of the mission".

The second job instruction step is to reduce the imported data set to only data that can be freely released into a permanent, free, and irrevocable public archive. This step requires the Packager to reference the source data license limitations. Any data that does not meet the requirements is eliminated from the imported data.

The third job instruction step is to convert the content to publicly available open-source formats. In this case the maximum amount of meta-data about each file is included in the output dataset. This would include metadata referencing the source of the data, author (photographer, recorder, news feed etc.), time, date, geographic location, including license release requirements (copyrights for instance). The maximum amount of metadata about each data item is desirable to allow the public to utilize the public archive to the fullest extent possible.

The fourth job instruction step is to Export the dataset. There are many ways to Export a Public Archive dataset. One option is to simply produce a URL (Universal Resource Locator) to the dataset still residing inside the Packager device. This option would require the Packager device to be publicly accessible via an online communications channel such as the Internet. This is an undesirable methodology as the Packager is then open to potential cyberattack since it would need to be directly connected to Internet Public access.

Another option is to output the dataset to hard media such as DVD disks. Alternately, the dataset could be packaged into a public open-source format, for example a .zip file of the entire dataset. The entire dataset could then be allowed or requested to Export the dataset to some public archive, say the Smithsonian Institute, or NASA. These institutions would make Public Access available to the dataset.

One of the best options for Export is to Export the dataset to a Public/Private Blockchain. In this case, the record becomes irrevocable, as long as the Blockchain resource remains in existence. The dataset located in a Public/Private Blockchain allows worldwide could allow access to the dataset on a read-only basis.

Additionally, Export of the dataset could include job instruction set specifications to Export the dataset as a non-fungible token (NFT). This would include any of the desired specifications for securitization of the content of the dataset, and the creation of ownership credentials of the NFT itself. The NFT could include the entire dataset embedded into the NFT token. Alternately, the NFT may contain a URL, pointer, or link to the actual dataset location. The NFT could include embedded access credentials to allow seamless access to the dataset. The point illustrated herein is the capability of the Packager to functionally act upon the dataset according to a stepwise process described in the job instruction set specifications.

The fifth and last job instruction step is to produce a record of the job specifications and completion information. This includes a log of the statistics of the work done by the Packager, and the location of the Exported dataset. This information may be kept locally to the Packager, or Exported to the Big Data Cluster dB. This information may be further Exported to a Public or Private Block Chain to create a more durable record of the Packager work product.

We claim:

1. One or more devices comprising at least one computer processor that acquires and processes human biological change data from event data stream(s) that allows for ranking one or more changes in said biological change data and correlates said biological change data with ranking statistics from an event and wherein said correlation identifies and measures a magnitude of change of said human biological responses from data acquired from said event data stream(s) so that correlation of said biological change data with said ranking statistics creates one or more objects for storage and analysis within in one or more databases, wherein said objects possess time synchronized temporal human biological responses before, during or after an event and wherein said objects also possess biological change data that utilizes correlation of said biological change data with said ranking statistics and results in objects that also contain one or more ranked values of said human biological responses and wherein said biological change data is provided in data streams that are categorized by categories including audio, visual, audio-visual, olfactory, gustatory, and somatic parameters or any combination thereof which subsequently provide said data or data stream into a dynamically controlled digitized marketplace so that said data can be marketed and monetized by one or more individuals, entities, including artificial intelligence and/or systems that review and select one or more of said categories monetized by a valuation technique such that a first creation, entrance and retrieval of said biological change data provides an ability to assign an initial value of one or more nonfungible tokens, wherein said nonfungible token includes packeted biological change data based on demand for said categories in said marketplace and wherein said data is guaranteed and warrantied.

2. The nonfungible tokens of claim 1, wherein said captured biological change data is replicated only with permission to employ a unique at least one set of data stream signatures wherein said data stream signatures are securitized in that said data stream signatures are replete with certificates of authentication and authorization and wherein dynamically changing values reside both within and external to digital marketplaces as said human change data is captured via data streams and/or when said data streams enter one or more digital marketplaces wherein a user can monetize one or more non-duplicatable data streams.

3. The nonfungible tokens of claim 1, wherein cryptographic keys and cryptographic check sums exist to provide commoditized encryption techniques that also utilize data stream signatures, wherein an owner of said tokens provides a set of constraints regarding contract, trading, and utilization constraints.

4. The one or more devices of claim 1, wherein a packager is included as a portion of said devices that extracts data from one or more data sets and wherein said data is contained in said data sets as data slices and/or other subsets of data that are optionally contained in said objects and that allow for selectivity of said data sets according to desired types and intensities of one or more biological changes of a magnitude determined and measured by said devices.

5. The packager of claim 4, wherein said objects are selected from one or more of a group consisting of fungible tokens (FTs), non-fungible tokens (NFTs), CDs, DVDs, memory storage devices, records, and printed tickets.

6. The packager of claim 5, wherein said packager feeds data for a digitized marketplace such that a transaction takes place by utilization of said data slices such that unique content is captured within said data slices and wherein said packager further provides constraints, limitations, and transactions that are securitized and ephemeralized.

7. The nonfungible tokens of claim 1, wherein monetization is achieved by valuation of an acquisition of desirable and accessible packaged data in specific time intervals wherein any individual(s), organization(s), or other real and/or virtual entities can acquire/purchase said data and/or data streams in specific time intervals that allows for access, iteration, and experiential interaction by obtainment of a desirable set of packaged data upon request with a form of monetary payment that is monetization.

8. The nonfungible tokens of claim 1, wherein desirable packaged data is captured as real or virtual events and includes events comprising; sporting events, historical events, private and public memorabilia, collections of coins, art, minted paper, stamps, digitized versions of internal and external architecture that includes rooms and offices in homes and businesses, and real and/or virtual items of value which are offered for payment via monetization.

9. The desired packaged data and data streams of claim 8, wherein said packaged data and data streams are provided in a digitized format that captures textural and binary content including chemical, biological, genetic, electrical, mechanical, artificial intellect, and quantum formulations in a form of data.

10. The desired packaged data and data streams of claim 9, wherein purchase of said packaged data and data streams in specific time intervals are sold as tokens and/or stored data retrieved from one or more real and/or virtual devices.

11. The devices of claim 1, wherein said devices must be able to compensate for bidding and an ability to fractionalize an asset and expose said asset within a digitized dynamically changing marketplace.

12. The one or more devices of claim 1, wherein said objects are tangible, real, physical objects.

13. The one or more devices of claim 1, wherein said objects are intangible and/or virtual objects.

14. The one or more devices of claim 1, wherein said objects are cryptographically secured, assigned ownership, and sealed such that an ownership record is generated.

15. The one or more devices of claim 1, wherein an ownership record is stored in an irrevocable database.

16. The one or more devices of claim 1, wherein said devices comprise a correlator/decider portion that includes one or more devices that triggers said rankings such that a content value is generated and wherein said rankings correlates with a change in sign, and magnitude of said human biological changes are determined and wherein said correlation provides a value of at least one segment of said event stream.

17. The one or more devices of claim 1, wherein said ranking statistics of an event stream utilizes game rules with multiple human referees and judges during a multitude of time synchronized human biological responses during said event data stream.

18. The one or more devices of claim 1, wherein said value of a segment of an event data stream triggers generation of a contract for ownership of a determined valuable segment of said event data stream, an actual event, or attributes of an event wherein said event data stream(s) identifies, captures, quantifies, ascertains, analyzes and packages human biological reaction data.

19. The one or more devices of claim 1, wherein said devices exist in or within an intranet, internet, or cloud data handling system so that said devices can function in conjunction with computers that have access to computer networks.

20. The one or more devices of claim 1, wherein said biological state can be captured instantaneously or after an event that influences and/or causes said biological state and wherein said biological state includes a biological response state of existence and wherein said biological state is temporal in that past and present data is available for collection and analysis and eventual prediction of future biological states at any time by a user of said one or more devices.

21. The one or more devices of claim 1, wherein said devices and objects are selected from at least one of a group consisting of smart phones, video and/or digital cameras, tickets, and tokens and wherein individuals can share at least one of a group consisting of a common grouping, location, language and understanding of an event or events that is observed and/or within which said individuals are participating.

22. The one or more devices of claim 1, wherein input data is collected via a data collection funnel such that a data funnel can function as a device that collects data which includes associated time stamps and geo location features.

23. The one or more devices of claim 1, wherein data flows along a directed flow path toward a Big Data Cluster device that accepts and associates data and data streams via a data associator, organizes via a data organizer, and stores data in a database and wherein said Big Data Cluster device includes a database which contains data content provided in audio, video and/or audio/visual and textural data over a specified time interval wherein said Big Data Cluster device includes a time ordered time interval and wherein said Big Data Cluster device includes a data organizer that associates data with a data associator wherein all data from all points of origin creates multiple tracks of data for each of any original source data inputs that reside in said Big Data Cluster such that a locater provides a location and address for said data inputs to reside and wherein said data source inputs within said locater provides complete available information regarding location, perspective viewing angles, distances and recording instruments of events so that said data sources are now also organized and located in data tracks wherein each data track is streamed data that includes at least geolocations, movement, angles, and recording capabilities of one or more events so that said data tracks themselves can be further analyzed.

24. The devices of claim 1, wherein an aligner provides time synchronization of and for various events captured as data streams wherein said aligner gives preferential integrity to said data streams and wherein in addition said aligner adjusts for geolocation and recording delays associated with each data stream at a specific geolocation wherein said aligner also produces a time synchronizer that provides instantaneous time along each input data stream.

25. The one or more devices of claim 1, wherein an identifier/quantifier is utilized as an intelligent comparator processor that leverages data in said Big Data Cluster to determine data points of interest that occur at any time associated with said events.

26. The one or more devices of claim 1, wherein as data and data streams are created, collected, and organized, an intelligent comparator processor with an intelligent comparator identifier and an intelligent comparator quantifier is employed so that said data and data streams can be utilized and provided as storage vectors of time with synchronized tensors of expressed precursors of a quantifiable change in biological reactions, wherein said tensors are a data structure used in linear algebra that include vectors and matrices allow for calculation of arithmetic operations with said tensors wherein said tensors are also a generalization of matrices represented using n-dimensional arrays wherein data is further processed with a biological comprehender/editor that allows for analysis of one or more sentiment intensities during specific times and/or time intervals during said event and sums all said data and data streams in columns biological response s that can be summed and tabulated at any instant in time or time interval to produce a consistent record of any biological intensity that occurs across an entire event.

27. The comprehender/editor of claim 26, wherein said comprehender/editor also provides a scale that yields a biological score from an elevated positive value to a lower ranking negative value such that values and associated ranks are assigned based upon biological reactions of one or more individuals in relation to themselves and each of other individuals wherein production of biological intensity values is tracked, captured and is ultimately editable by an editor portion of said comprehender/editor to provide an adjustable output of an edited version of raw biological change intensity data along associated data tracks.

28. The one or more devices of claim 1, wherein a predictor is included that provides a neural network and artificial intelligence iterator and algorithm predictions that utilize an entire data set ultimately obtained from an adjustable output of edited versions of said raw biological change intensity data along data tracks.

29. The predictor of claim 28, wherein said predictor predicts biological states by inputting data into its neural network and wherein said predictor trains and retrains itself by utilizing continuous data processing feedback loops to produce outputs that match said edited versions of raw biological change data intensity along data tracks and wherein said feedback loops iterates until predicted results match manually edited results.

30. The predictor of claim 28, wherein said training and retraining is data that is captured in a memory of said predictor and every time a new data set is accessed, utilized, organized, and analyzed within or external to said one or more databases iteration of said data along data streams reaches a more precise satisfactory representation of actual biological response(s).

* * * * *